(12) United States Patent
Bedding et al.

(10) Patent No.: US 8,197,842 B2
(45) Date of Patent: *Jun. 12, 2012

(54) DIETARY SUPPLEMENT AND METHOD

(75) Inventors: Peter M. J. Bedding, Devon (GB); Franklin L. Pellegrini, Streetsboro, OH (US)

(73) Assignee: Freedom Health, LLC, Aurora, OH (US)

( * ) Notice: Subject to any disclaimer, the term of this patent is extended or adjusted under 35 U.S.C. 154(b) by 7 days.

This patent is subject to a terminal disclaimer.

(21) Appl. No.: 12/702,706

(22) Filed: Feb. 9, 2010

(65) Prior Publication Data

US 2010/0136044 A1 Jun. 3, 2010

Related U.S. Application Data

(60) Division of application No. 11/500,835, filed on Aug. 8, 2006, now Pat. No. 7,658,964, and a continuation-in-part of application No. 10/435,367, filed on May 9, 2003, now Pat. No. 7,824,706.

(51) Int. Cl.
| | |
|---|---|
| *A23K 1/17* | (2006.01) |
| *A23K 1/165* | (2006.01) |
| *A23K 1/18* | (2006.01) |
| *A23K 1/00* | (2006.01) |
| *A61K 47/00* | (2006.01) |
| *A61K 9/28* | (2006.01) |
| *A61K 9/68* | (2006.01) |
| *A23L 1/20* | (2006.01) |
| *A23D 7/00* | (2006.01) |

(52) U.S. Cl. ........ 424/442; 424/439; 424/438; 424/441; 424/440; 426/630; 426/635; 426/601; 426/808

(58) Field of Classification Search .................. 424/442, 424/439, 438, 441, 440; 426/630, 635, 601, 426/807

See application file for complete search history.

(56) References Cited

U.S. PATENT DOCUMENTS

| | | | |
|---|---|---|---|
| 4,729,896 A | 3/1988 | Sawhill | |
| 4,820,731 A | 4/1989 | Mascioli et al. | |
| 4,950,656 A | 8/1990 | Lichtenberger | |
| 5,312,636 A * | 5/1994 | Myllymaki et al. | .......... 426/417 |
| 5,320,846 A | 6/1994 | Bistrian et al. | |

(Continued)

FOREIGN PATENT DOCUMENTS

EP 1361264 A1 12/2003

(Continued)

OTHER PUBLICATIONS

Hallfrisch et al. "Diet containing soluble oat extracts improve glucose and insulin responses of moderately hypercholesterolemic men and women", Am J Cln Nutr, 1995;61:397-84.*

(Continued)

*Primary Examiner* — Isis Ghali
(74) *Attorney, Agent, or Firm* — Reinhart Boerner Van Deuren s.c.

(57) ABSTRACT

A novel dietary supplement and methods for the manufacture of the same are disclosed for feeding to equines and other animals. The dietary supplement of the present invention is beneficial to the health of equines and other animals. The dietary supplement of the present invention consists of safe and natural ingredients rather than drugs, and is orally administrable. The ingredients of the dietary supplement make the dietary supplement of the present invention highly beneficial to the health of equines and other animals.

19 Claims, 1 Drawing Sheet

U.S. PATENT DOCUMENTS

| | | | |
|---|---|---|---|
| 5,505,968 | A | 4/1996 | Schaefer et al. |
| 5,589,186 | A | 12/1996 | Isobe et al. |
| 5,660,852 | A | 8/1997 | McKeown et al. |
| 5,716,639 | A | 2/1998 | Carlsson et al. |
| 5,759,537 | A | 6/1998 | Garnett |
| 5,972,985 | A | 10/1999 | Thomas et al. |
| 6,019,995 | A | 2/2000 | Steensma |
| 6,020,324 | A | 2/2000 | Jamas et al. |
| 6,045,834 | A | 4/2000 | Howes et al. |
| 6,117,458 | A | 9/2000 | Morgan |
| 6,156,355 | A | 12/2000 | Shields et al. |
| 6,200,624 | B1 | 3/2001 | Mazer et al. |
| 6,203,818 | B1 | 3/2001 | Vester |
| 6,329,414 | B1 | 12/2001 | Thomas et al. |
| 6,344,221 | B1 | 2/2002 | Evans |
| 6,355,693 | B1 | 3/2002 | Herslof et al. |
| 6,410,067 | B1 | 6/2002 | Kanter et al. |
| 6,451,370 | B1 | 9/2002 | Anderson |
| 6,537,544 | B1 | 3/2003 | Lonner et al. |
| 6,759,064 | B2 | 7/2004 | Morre et al. |
| 2002/0044988 | A1 | 4/2002 | Fuchs et al. |
| 2003/0153746 | A1* | 8/2003 | Van Lengerich et al. ........................ 536/123.12 |
| 2003/0165604 | A1 | 9/2003 | Tsubaki et al. |
| 2004/0115309 | A1 | 6/2004 | Harris |

FOREIGN PATENT DOCUMENTS

| | | |
|---|---|---|
| JP | 50-5568 | 5/1973 |
| JP | 61-009255 | 1/1986 |
| JP | 06-209719 | 2/1994 |
| JP | 09-262061 | 10/1997 |
| JP | 2004051582 | 12/2004 |
| WO | 9839980 | 9/1998 |
| WO | 9901044 | 1/1999 |
| WO | 9902041 | 1/1999 |
| WO | 9918188 | 4/1999 |
| WO | 9953772 | 10/1999 |
| WO | 0117366 | 3/2001 |
| WO | 0174173 | 10/2001 |
| WO | 2005002367 | 1/2005 |

OTHER PUBLICATIONS

Bengmark et al. "Gastroinstestinal surface protection and mucosa reconditioning"; JPEN J Partenter Enteral Nutr. Sep.-Oct. 1995; 19(5)'410-5.*

Bell, S; Goldman, VM; Bistrian, BR et al. "Effect of beta-glucan from oats and yeast on serum lipids". Crit Rev Food Sci Nutr 1999; 39:189-202 [review].

Braaten, JT; Scott, FW; Wood, PJ et al. "High beta-glucan oat bran and oat gum reduce postprandial blood glucose and insulin in subjects with and without type 2 diabetes". Diabet Med 1994; 11:312-8.

Czop, JK. "The role of beta-glucan receptors on blood and tissue leukocytes in phagocytosis and metabolic activation". Pathol Immunopahtol Res 1985; 5:286-96.

Estrada, A; Yun, CH; Van Kessel, A et al. "Immunomondulatory activities of oat beta-glucan in vitro and in vivo." Microbiol Immunol 1997; 41:99 1-8.

Bolm, N; Kulicke, W. "Rlzeological studies of barley (1-3)(1-4) beta-glucan in concentrated solution". Carbohydrate Research, 1999, 315, 293-301.

Spittler, RE; Oehler, A. "Glutamine: Effects on the immune system, protein balance and intestinal functions". Wien Klin Wochenshr. 1996; 108(2):667-8.

Vazquez, P; Gomez DE Segura, IA; Cos, A; Candela, CG; De Miguel, E. "Response of the intestinal mucosa to different enteral diets in situations of surgical stress and malnutrition". Nutr Hosp. Nov.-Dec. 1996; 11 (6):321-7.

Bertolo, RF; Chen, CZ; Law, G; Pencharz, PB; Ball, RO. "Threonine requirement of neonatal piglets receiving total parenteral nutrition is considerably lower than that piglets receiving an identical diet intragastrically". J. Nutr. Oct. 1998; 128(10):1752-9.

Ball, RO; Law, G; Bertolo, RFP, Pencharz, PB. "Adequate oral threonine is critical for mucin production and mucosal growth by neonatal piglet gut". Proceedings of the VIIIth International Symposium on Protein Metabolism and Nutrition, EAAP, 1999.

Marshman, E; Booth, C; Potten, CS. "The intestinal epithelial stem cell". Bioessays Jan. 2002; 24(1):91-8.

Lin, Cheng-Mao. "Effect of dietary nucleotide supplementation on in vivo and in vitro immune function in protein-malnurished mice". University of Florida, PhD. Dissertation, Dec. 1995.

IP, WK; Lau, YL. "Role of mannose-binding lectin in the innate defense against *Candida albicans*: Enhancement of complement activation, but lack of opsonic function, in phagocytosis by human dendritic cells". J Infect Dis Aug. 1, 2004; 190(3):632-40. Epub Jun. 28, 2004.

Swanson, KS; Grieshop, CM; Flickinger, EA; Healy, HP; Dawson, KA; Merchen, NR; Fahey, GC JR. "Effects of supplemental fructooligosaccharides plus mannanoligosaccharides on immune function and ileal and fecal microbial populations in adult dogs". Arch Tierernahr. Aug. 2005; 56(4):309-18.

Davis, E; Maxwell, C; Kegley, B; De Rodas, B; Friesen, K; Hellwig, D. "Efficacy of mannan oligosaccharide (bio-mos) addition at two levels of supplemental copper on performance and immunocompetence of early weaned pigs". Arkansas Animal Science Department Report 1999.

Bekers, M. et al.: "Oats and fat-free milk based functional food product"; Food Biotechnology, Dekker, New York, NY, US, 15(1), 1-12 (2001).

Miller, Alan L., MD, "Therapeutic considerations of L-Glutamine: A review of literature", www.thorne.com/altamedrev/fulltext/glutamine4-4.html, Dec. 2002, pp. 1-12.

Russett, DR. J.C., "Specialty products research notes: Lecithin and equine ulcers", Central Soya, LEC-H-55, Mar. 2002, pp. 1-10.

Lardy, Greg; Poland, Chip, "Feeding management for horse owners", AS-953, www.est.nodak.edu/extpubs/ansci/horse/as953w.htm, Feb. 2001, pp. 1-6.

Reynolds, Judith A., PhD, P.A.S., "Are you feeding your horse like a horse?", Moorman's Feed Facts, Oct. 2000, pp. 1-4.

Gren, T.; Hutchison, K.; and Kaufmann, P., "Oral lipid matrix in liquid-filled softgel capsules: A drug delivery system for improved oral bioavailability," Drug Delivery Technology, vol. 2, No. 7, Oct. 2002.

Winawer, Neil Md; Williams, Mark V. Md, Making health care safer: A critical analysis of patient safety practices; Chapter 33, University of California at San Francisco (UCSF)—Stanford University Evidence-based Practice Center, AHRQ Publication 01-E058, Jul. 20, 2001.

McClure, SR; Glickman, LT; Glickman, NW., Prevalence of gastric ulcers in show horses, J Am Vet Med Assoc 1999:215: 1130-1133.

Traub-Dargatz, JL; Kopral, CA; Seitzinger, AH; Garber, LP; Forde, K; White, NA. "Estimate of the national incidence of and operation-level risk factors for colic among horses in the United States", Spring 1998 to Spring 1999. J Am Vet Med Assoc, Jul. 1, 2001; 219(1):67-71.

Lorenzo-Figueras, M; Merritt, AM, Effects of exercise on gastric volume And pH in the proximal portion of the stomach of horses. An J Vet Res, 2002; 63:1481-1487.

Mair, T; Divers, T; and Ducharme, N., "Manual of Equine Gastroenterology". London: WB Saunders, 2002.

Mitchell, RD, "Prevalence of gastric ulcers in hunger/jumper and dressage horses evaluated for poor performance", Assoc Equine Sports Med, Sep. 2001.

Kronfeld, DS, "Speed limit", Dipl. ACVN, Dipl. ACVIM. Mar. 2003, Article#4212.

Pellegrini, F. "A large-scale necroscopy of equine ulcers", Submitted to Equine Veterinary Journal, 2004.

Martin, GP; Marriott, C; Kellaway, IW, "The interaction of progesterone with mucus glycoproteins", Pharm Acta Helv 1981; 56(1):5-8.

Kiviluoto, T; Paimela, H; Mustonen, H; Kivilaakso, E. Exogenous surface-active phospholipids protects necturas gastric mucosa against luminal acid and barrier-breaking agents:. Gastroenterology, Jan. 1991; 100(1):38-46.

McNeil, PL; Ito, S. "Gastrointestinal cell plasma membrane wounding and resealing in vivo". Gastroenterology, May 1989; 96(5 Pt. 1): 1238-48.

Dupree, JL; Coetzee, T; Blight, A; Suzuki, K; Popko, B (1998), "Myelin galactolipids are essential for proper node of Ranvier formation in the CNS". J Neurosci 18(5):1642-49.

Kreitler, B. "Feed and nutrition: Fat: The next nutraceutical?" Thoroughbred Times, Apr. 12, 2003.

Davidson, MH; Dugan, LD; Burns, JH et al. "The hypocholesterolemic effects of betaglucan in oatmeal and oat bran." A dose-controlled study. JAMA 1991 1991; 265:1833-9.

* cited by examiner

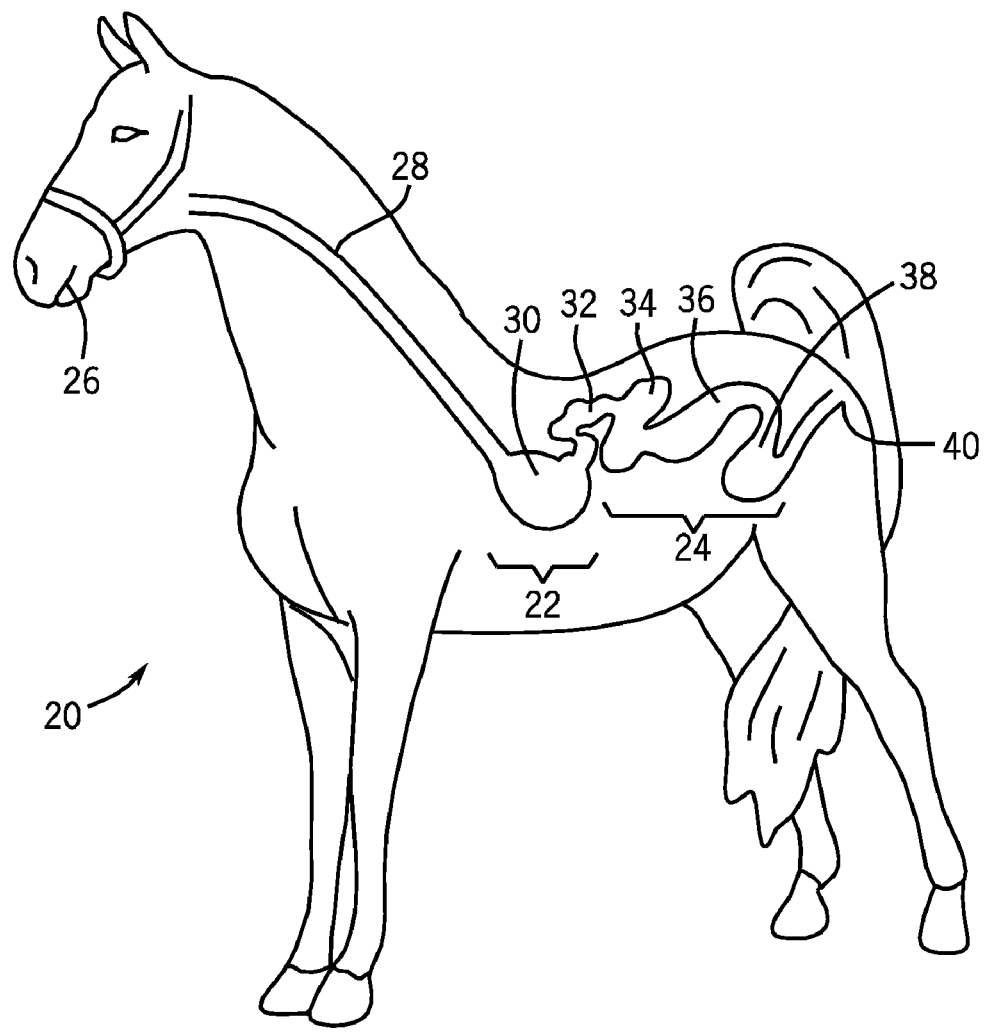

DIETARY SUPPLEMENT AND METHOD

CROSS REFERENCE TO RELATED APPLICATIONS

This patent application is a divisional patent application of U.S. patent application Ser. No. 11/500,835, filed on Aug. 8, 2006 now U.S. Pat. No. 7,658,964, entitled "Dietary Supplement and Method for Increasing the Colostrum Immunoglobulin Levels in Equine Mares," which patent application is assigned to the assignee of the present invention and is a continuation-in-part of U.S. patent application Ser. No. 10/435,367, filed on May 9, 2003 now U.S. Pat. No. 7,824,706, entitled "Dietary Supplement and Method for the Treatment and Prevention of Digestive Tract Ulcers in Equines and Other Animals," U.S. patent application Ser. No. 10/802,342, filed on Mar. 17, 2004, entitled "Nutritional Product and Method for Optimizing Nutritional Uptake in Equine Foals and Other Animals," and U.S. patent application Ser. No. 10/947,598, filed on Sep. 22, 2004, entitled "Dietary Supplement and Method for Treating Digestive System-Related Disorders," all three of which patent applications are assigned to the assignee of the present invention and which are hereby incorporated herein by reference in their entirety.

BACKGROUND OF THE INVENTION

Field of the Invention

The present invention relates generally to a dietary supplement for equine mares and other animals, and more particularly to a novel dietary supplement for feeding to equine mares and other animals prior to parturition to boost the colostrum immunoglobulin level in lactating equine mares and other animals and thereby enhance the passive transfer of immunity to neonatal equine foals and other neonatal animals.

As with any young mammal, the equine foal has special nutritional requirements which are required in order to optimize its health and growth rate. This is particularly the case if the foal is intended to become a performance horse, either a racehorse or a show horse. While genetics and environmental conditions undoubtedly play a significant role in the growth and development in determining the growth potential of each foal, nutrition must also be taken into account and is certainly of vital importance in the health, growth, and development of foals and young horses.

As such, feeding the foal and the young horse, particularly in conjunction with the variables associated with a lactating mare, is a matter requiring careful balance which must be taken seriously. The interaction of genetics, environment, management, and nutrition of the foal and the mare is quite complex. It has been determined that the nutrition and the immunoglobulin antibodies that a foal receives initially will have a profound and long-term effect on the health, development, and soundness of the foal for its entire lifetime.

Under normal conditions, the mare will hopefully produce enough milk for the foal, typically about fifteen liters per day. While this should provide sufficient nutrition for the foal to develop, there are a number of factors that can disturb the balance and result in the foal receiving insufficient nutrition to grow and develop properly. It is essential that the foal ingest "first milk" or colostrum which is produced by the mare for approximately the first twelve hours after giving birth and which provides the foal with the important immunoglobulin antibodies which enable it to resist infections and which protect it from a variety of diseases. This ingestion of colostrum is called "passive transfer."

The immunoglobulin antibodies in the colostrum or "first milk" are capable of protecting the foal from infection during its first months of life, and are necessary because the foal doesn't begin to produce these immunoglobulin antibodies until after it is born. Therefore, passive transfer of immunoglobulin antibodies from the mare to the foal through ingestion of the colostrum is necessary to ensure that the newborn foal will have a defense against infections until the foal's own immune system begins to produce antibodies. The colostrum is produced in the mare's udder during the last two to four weeks of gestation in response to hormonal changes, and it is only produced once during the mare's pregnancy. The colostrum is replaced with normal milk within approximately twelve hours from the time the foal first suckles. Good quality colostrum is typically sticky, thick, and yellow, although its appearance can be misleading and thus should not be the only factor used in order to determine whether passive transfer has occurred.

Upon ingestion of the colostrum by the foal, special cell tissue which are contained in its intestinal mucosa of the foal's foregut will absorb and transmit the immunoglobulin antibodies contained in the colostrum into the blood of the foal. The immunoglobulin antibodies are absorbed through pores contained in special cells in the gut wall into the bloodstream of the foal during the six to eight hour period immediately after the foal is born. By the end of this relatively short time period, these cells in the foal's intestinal mucosa are replaced with cells in the intestinal mucosa of the foal's foregut which have pores that are too small for the immunoglobulin antibodies to pass therethrough. At this point, the size of the immunoglobulin antibodies prohibit their transfer through the smaller ores in the cells of the intestinal mucosa of the foal's foregut and into the foal's bloodstream.

Thus, it is essential that the foal is suckling within the first two to six hours of its life, which is the time that the immunoglobulin antibodies are at a peak level of absorption in the intestinal mucosa of the foal's foregut. It is preferable that the foal is suckling within two hours of its birth to be absolutely certain of immunoglobulin antibody absorption, and it is a general principle that the earlier a foal suckles, the more immunoglobulin antibodies it will receive. The second general principle is that the higher the concentration of colostrum immunoglobulin antibodies produced by the mare, the more likely it is that a significant amount will absorbed through the special cells in the gut wall into the bloodstream of the foal during the critical six to eight hour period after the foal is born.

There are a number of factors which can cause either a reduced level of passive transfer or a failure of passive transfer. These factors include poor colostral quality (insufficient immunoglobulin antibodies contained in the colostrum, early production of colostrum by the mare prior to foaling, low milk yield (which may be due to the mare losing her milk), low immunoglobulin antibody transfer as a result of poor feeding by the foal (sometimes due the mare refusing to allow the foal to suckle), malabsorption by the intestinal mucosa of the foal, and premature birth of the foal resulting in insufficient production of colostrum. Failure to obtain adequate passive immunity occurs in fifteen percent or more of thoroughbred and standardbred foals, with the outcome being an increase in morbidity and mortality. Even in thoroughbred foals, a six to eight percent loss rate is widely viewed as normal.

A foal's immune system is built up from the time of its birth, first due to the initial colostrum provided by the mare and later from environmental conditions. The immunity resulting from the immunoglobulin and the first antibodies are the most important immunity that a foal must acquire. During the early days of a foal's life, it will be invaded by bacteria, some of which are beneficial and will help in digestion, others of which are pathogens that will attempt to survive and produce toxins in the foal's body or cause diseases. During this time, the foal must begin to produce its own immunity defenses, and special cells will begin to be produced and to circulate in the blood to protect the foal's body from this invasion of pathogens.

On the ninth day after birth, the mare goes into heat, and foals are likely to get diarrhea at this time (this is referred to as foal's "scours"). Since the foal's scours typically occur at the same time as the mare goes into heat, it was long believed that the cause of the foal's scours was due to hormonal changes within the mare that was passed on to the foal through the milk. Scientific studies have disproved this as the root cause, suggesting instead that foal's scours is actually caused by changes within the foal's digestive system as it prepares to digest solid food. During the initial "gear-up" period too much fluids and enzymes are released for the large intestines to absorb, resulting in a light case of diarrhea.

In order to understand the next aspect of a foal's proper nutritional development, it is necessary to understand the basic principles of the digestive system of horses. While horses are monogastric (one stomach) animals, they are also hindgut fermenters, which means that they have relatively small stomachs and small intestines (collectively referred to as the foregut), and relatively large colons (collectively referred to as the hindgut). The relative volume of the foregut in horses is approximately thirty-five to forty percent of the total volume of the digestive tract. By comparison, the relative volume of the foregut in pigs is sixty to sixty-five percent of the total volume of the digestive tract, and the relative volume of the foregut in ruminant animals such as cows is eighty-five to ninety percent of the total volume of the digestive tract.

While the foregut of horses is relatively small, their stomachs are even smaller, representing only approximately one-quarter of the volume of the foregut, and thus approximately nine percent of the total volume of the digestive tract. In view of the small percentage of the digestive tract represented by the stomach, one might refer to a horse's stomach as a preparatory chamber. The principal consequence of this relatively small stomach size is that the rate of passage of feed through horses' stomachs is relatively fast, leaving relatively little time for the digestion process to occur. In addition, smaller feed particles pass through horses' foreguts even more quickly, with the time of passage of such smaller particles through the horses' stomachs potentially not allowing for proper digestion to occur.

The mare will pass on beneficial bacteria in her feces that the foal will nibble at and ingest, and these bacteria provide the foundation for the foal's own beneficial microflora. Under optimum conditions, these bacteria will flourish, and will enable the foal to begin to use its hindgut and eventually to become a full-fledged hindgut fermenter. This process takes many months, and will not be complete until the foal is at least a year old, at which time it has become a fully efficient hindgut fermenter.

Since the foal's digestive system is not fully ready to perform the anaerobic activity necessary to digest solid food for some time, grain eaten by the foal may pass through the foal's foregut and into the horse's hindgut without being properly digested. This can cause a highly acidic environment that can lead to colonic ulceration. In addition, as the pH drops, normal fauna (*lactobacillus* and *streptococcus bovis* colonies) may be replaced by harmful bacteria.

During the first six months of this period, it is desirable that the mare's diet be controlled, and that the mare's own hindgut microflora are looked after and that any pathogens or mycotoxins that are ingested are not allowed to proliferate or enter the mare's blood stream and affect milk quality or quantity. These pathogens and mycotoxins should not be allowed to be passed over to the foal. As such, functional feeding of both the mare and the foal is important, and will help support the beneficial microflora in their respective hindguts.

Functional feeding of the mare after parturition may be accomplished by using the dietary supplement disclosed in U.S. patent application Ser. No. 10/435,367, filed on May 9, 2003, entitled "Dietary Supplement and Method for the Treatment and Prevention of Digestive Tract Ulcers in Equines and Other Animals." A section related to the background of the use of this nutritional supplement in treating and preventing ulcers in equines and other animals is included as an appendix that is located at the specification. The dietary supplement and nutritional aid and methods for the manufacture and administration of the same disclosed in that patent application are efficacious in the treatment and/or prevention of digestive tract ulcers in horses and other animals. That dietary supplement is effective in treating and/or preventing gastric ulcers, and in treating colonic ulcers as well. That dietary supplement consists of safe and natural ingredients rather than drugs, and is orally administrable. The ingredients of that dietary supplement when combined provide a synergistic efficacy which greatly exceeds the sum of the efficacies of the individual ingredients, making the dietary supplement highly effective in the treatment of digestive tract ulcers.

Functional feeding of the foal after birth may be accomplished by using the nutritional supplement disclosed in U.S. patent application Ser. No. 10/802,342, filed on Mar. 17, 2004, entitled "Nutritional Product and Method for Optimizing Nutritional Uptake in Equine Foals and Other Animals." The nutritional product and methods for the manufacture and administration of the same disclosed in that patent application is effective in supporting the growth and health of equine foals, and in supporting and stimulating its immune system as well. That nutritional product consists of safe and natural ingredients rather than drugs, and is orally administrable. The ingredients of that nutritional product when combined provide a synergistic efficacy which greatly exceeds the sum of the efficacies of the individual ingredients, making the nutritional product highly effective in promoting and enhancing the growth, nutritional uptake, and immune system of equine foals.

One additional factor in the health of newborn foals is the health of the mare during gestation. In particular, if the mare has harmful bacteria such as *E. coli* or *Salmonella*, they will almost certainly be passed from the mare to the foal. Such bacterial can result in foal's scours, endotoxemia, septicemia, and enteric infections. Accordingly, it will be appreciated that the health of the mare and particularly the freedom of the mare from such bacteria is critical to the health of the neonatal foal.

It is accordingly the primary objective of the dietary supplement of the present invention that it provide a substantial increase in the levels of immunoglobulin antibodies in the colostrum or "first milk" produced by a mare immediately upon parturition. In this regard, it is an objective of the dietary supplement of the present invention that it provide not less than a fifteen percent increase in the level of immunoglobulin antibodies in the colostrum. It is a related objective of the dietary supplement of the present invention that it result in a substantial enhancement in the passive transfer of immunoglobulin antibodies from the mare to the foal through ingestion of the colostrum.

The other principal objective of the dietary supplement of the present invention is that it strengthen the immune system of the mare during gestation. It is a related objective that it help protect the mare's intestinal mucosa from aggressive actions of potentially dangerous substances and pathogens during gestation to prevent harmful bacteria from being passed on to the foal. It is an additional objective of the dietary supplement of the present invention that it consist entirely of safe and natural ingredients rather than drugs. It is a still further objective of the dietary supplement of the present invention that it be orally administrable, thereby making its dispensation a simple matter.

The dietary supplement of the present invention must also be both stable and have a commercially acceptable shelf life, and it should also require no special care to be provided by the user throughout its shelf life prior to usage. In order to enhance the market appeal of the dietary supplement of the present invention, it should also be relatively inexpensive when compared to previously known nutritional supplements given to mares and other animals prior to parturition to thereby afford it the broadest possible market. Finally, it is also an objective that all of the aforesaid advantages and objectives of the dietary supplement of the present invention and its method of administration be achieved without incurring any substantial relative disadvantage.

SUMMARY OF THE INVENTION

The disadvantages and limitations of the background art discussed above are overcome by the present invention. With this invention, a novel dietary supplement that is specifically formulated to increase the immunoglobulin antibody level in colostrum produced by equine mares and other animals at parturition is provided. Through the administration of this dietary supplement to equine mares and other animals during approximately the last ninety days of gestation, the level of immunoglobulin antibodies is substantially increased, thereby allowing an enhanced level of passive transfer of the immunoglobulin antibodies to foals, thereby enhancing their immune systems and protecting them against a number of conditions that could otherwise adversely affect the health of foals. As will rapidly become apparent to those skilled in the art, the dietary supplement of the present invention is more than the sum of its ingredients, with the combination of ingredients yielding a synergistic result more efficacious than the results which would be produced if each of the ingredients acting by itself were provided to mares or other animals during gestation.

In its basic form, the dietary supplement of the present invention includes four principal components, each of which provides a beneficial effect which is facilitated by the inclusion of a particular ingredient or a mixture of ingredients in the dietary supplement. The first principal ingredient is a polar lipid supplement that preferably contains significant amounts of polar lipids and antioxidants, and that enhances growth and strengthens the immune system. The polar lipid supplement acts as an emulsifier which will facilitate the absorption of water-soluble and fat-soluble nutrients (and drugs) to into the bloodstream. The polar lipid supplement also is high in polar lipids which protect and strengthen the intestinal and tissue of the digestive system and augment the protective effect of mucus in the digestive tract. Polar lipids also form the membranes of neurons and their sheathing.

In the preferred embodiment, the polar lipid supplement contains at least a substantial portion of oat oil (of which polar lipids make up approximately twenty-five percent of the oat oil), which contains a high concentration of polar lipids and antioxidants. Optionally, other oils such as sunflower oil (preferably) or soybean oil, olive oil, palm oil, corn oil, rapeseed oil, linseed oil may be contained in the blend of ingredients contained in the polar lipid supplement. A form of the dietary supplement which is to be compounded in a paste form may contain some sunflower oil as a carrier, and a form of the dietary supplement which is to be compounded in a liquid form may contain a greater amount of sunflower oil (sunflower oil is a thinner oil and does not contain as high an amount of polar lipids). Less or no sunflower oil will be included in the dietary supplement if it is to be compounded into a granular or solid form.

The second principal ingredient of the dietary supplement of the present invention is soluble beta-glucan fiber, which is thought to be the most potent stimulator of the immune system. Beta-glucans are polysaccharides that also extract LDL cholesterol (the bad cholesterol) from the digested foodstuffs and lead to their excretion from the body, thereby reducing the fraction of LDL cholesterol in the bloodstream. They also sequester sugars and release them over a period of time, reducing sugar highs and lows to thereby stabilize blood sugar. Beta-glucans also slow the passage of foodstuffs through the digestive system.

In the preferred embodiment, the beta-glucan used is the soluble fiber in oats, an oligosaccharide that is found in the kernel of oats and is a powder when dried. It is a jelling agent that has an increased jelling effect when exposed to water, and also has a beneficial spreading effect that spreads the dietary supplement on the inner surface of the stomach. It also activates the protective macrophages to fight infections and increase the immune system. Beta-glucan is a nutrient for the beneficial bacteria of the hindgut, and helps the bacteria produce required micronutrients. Alternative sources of the beta-glucan are barley, yeast, and other vegetable sources.

The third principal ingredient of the dietary supplement of the present invention is at least one, and potentially two or more, amino acids, that increase the mare's native ability to enhance growth and to strengthen the immune system. Amino acids are nutricines which exert a beneficial effect on health rather than contributing directly to nutrition. Some amino acids increase the integrity of the digestive mucosa and are particularly beneficial to a stressed digestive system. Examples of amino acids which can be utilized in the dietary supplement of the present invention to provide this beneficial effect are glutamine and threonine. In the preferred embodiment of the dietary supplement of the present invention both glutamine and threonine are included.

Glutamine is a muscle fuel and also supplies nitrogen to the immune cells of the intestinal mucosa, which help to prevent pathogenic organisms from entering the circulatory system. Glutamine is considered to be a conditionally essential amino acid under normal conditions, because the body can create as much as is needed without the intake of glutamine supplements. When the digestive system is stressed, large amounts of glutamine are consumed, and supplements may be needed to replenish the supply. Glutamine also functions to "kick start" the formation of nucleotides, which, as mentioned above, are involved in the production of cell tissue and the maturation of the intestinal mucosa, and are directly involved in the immune processes and the energy systems. A diet deficient in glutamine will most likely also be deficient in nucleotides.

In the dietary supplement of the present invention, pure L-glutamine is used as the source of glutamine. L-glutamine is a naturally produced amino acid that is produced by breaking down a protein.

Threonine is a naturally produced essential amino acid and is an important component of the chemical pathway that creates mucin produced by the goblet cells distributed throughout the intestinal tract. By assisting metabolism and nutrient absorption, threonine contributes to a smoothly functioning digestive tract. A deficiency of threonine slows the regeneration of the gut wall and depresses the production of mucus. Threonine is especially useful for wound healing and for treating stress, but it is also an essential link in the production of immunoglobulins. In the dietary supplement of the present invention, pure L-threonine is used as the source of threonine.

The fourth principal ingredient of the dietary supplement of the present invention is mannan oligosaccharides (MOS), which are complex sugars that are used to bind pathogens and, at the same time, nourish beneficial bacteria. Although the mechanism is not well understood, mannan oligosaccharides seem to bind to attachment sites on pathogenic bacteria, preventing the pathogenic bacteria from binding to receptors in the enterocyte membrane. In the dietary supplement of the present invention, the mannan oligosaccharides are naturally derived from the cell wall of *saccharomyces cerevisiae* (brewer's yeast), a yeast extract, although other sources of mannan oligosaccharides are also acceptable. In addition to binding pathogenic bacteria, a mycotoxin absorbant also based upon *saccharomyces cerevisiae* may also be used to absorb or soak up mycotoxins in the colon.

The ingredients of the dietary supplement of the present invention which absorb or soak up mycotoxins and/or attract and eliminate pathogens are nutricines which may be made from *saccharomyces cerevisiae* (brewer's yeast). In the preferred embodiment, an estrified yeast cell wall mycotoxin absorbant such as the material marketed under the registered trademark MYCOSORB by Alltech, Inc. of Nicholasville, Ky., may be used to absorb or soak up mycotoxins in the colon. Additionally, in the preferred embodiment, a non-estrified yeast cell wall pathogenic bacteria absorbant such as the material marketed under the registered trademark BIO-MOS by Alltech, Inc., may be used to attract and eliminate pathogens.

In order to thicken the dietary supplement and keep the various constituents of the dietary supplement from separating, in the preferred embodiment an emulsifier is also used. One such emulsifier is guar gum (also known as guaran), a galactomannan which is extracted from the seed of the leguminous shrub *Cyamopsis tetragonoloba*. Guar gum is commonly used as an emulsifier, a thickener and a stabilizer. As such, it is not an active ingredient of the dietary supplement of the present invention.

In the preferred embodiment of the dietary supplement of the present invention, one or more additional ingredient may be included. One such additional ingredient is nucleotides, which are a nutricine that controls the regulatory pathways in growth and strengthen the immune system. Nucleotides are essential for cell division, when the chromosomes must be replicated. Nucleotides are typically created de novo, but they may be scavenged from the digesta in times of stress. A lack of dietary nucleotides will restrict both the growth and thickness of the intestinal wall. Nucleotides support nutrient uptake during growth periods, and are also critical during and after disease or tissue injury, helping to rebuild damaged tissue such as, for example, after chronic diarrhea. The nucleotides will also help in recovery after weight loss caused by disease or protein deprivation due to sickness.

Although not included in the preferred embodiment, the dietary supplement of the present invention also optionally include vitamins and/or mineral supplements. For example, Vitamin E can be added to the supplement, as can various minerals such as Selenium, Copper, Manganese, Zinc, and Chromium. These ingredients contribute to the dietary supplement in their capacity as antioxidants and assist in the total nutritional picture.

The dietary supplement of the present invention can be manufactured in several different forms, many of which may be added to feed. For example, the dietary supplement of the present invention may be manufactured as a solid (typically pelleted), as a granulated solid, as a powder, as a paste, or as a liquid. By adding oil (sunflower oil may be used as a carrier), the mixture can be brought to a paste having the consistency of peanut butter. By adding still more oil, the mixture can be made into a viscous liquid. The liquid or paste form of the dietary supplement of the present invention may be stored in gelatin capsules (as gelcaps), which make for a consistent dosage of the dietary supplement. In the paste form, the dietary supplement oral may be administered using a dose syringe.

Finally, it may be manufactured as a solid (typically pelleted), as a granulated solid, or even as a powder. In order to manufacture it as a solid, a small amount of oat bran or oat flour (or substitutes therefor) may be added to thicken it. By adding a higher percentage of oat bran or oat flour while stirring the mixture, a granular form of the supplement may be manufactured. By adding still more flour, a powder form of the supplement may be manufactured. The pelleting procedure should be performed at low temperature, preferably not higher than 65 degrees Celsius, and may optionally include approximately twenty percent by weight of grass meal and/or Alfalfa meal.

It is desirable that the dietary supplement of the present invention is taken on a regular basis, which in the preferred embodiment is daily or multiple times daily (for example, with meals). Upon disclosure of the dietary supplement of the present invention to those skilled in the art, they will immediately appreciate that the dietary supplement is much more than merely the sum of its ingredients. The combination of ingredients yields a synergistic result substantially more efficacious than a sum of the results which would be produced if each ingredient by itself was used.

It may therefore be seen that the present invention teaches a dietary supplement that provides a substantial increase in the levels of immunoglobulin antibodies in the colostrum or "first milk" produced by a mare immediately upon parturition. The dietary supplement of the present invention provides as much as a ninety-two percent increase in the level of immunoglobulin antibodies in the colostrum. The dietary supplement of the present invention also provides a substantial enhancement in the passive transfer of immunoglobulin antibodies from the mare to the foal through ingestion of the colostrum.

The dietary supplement of the present invention strengthens the immune system of the mare during gestation. The dietary supplement of the present invention also helps to protect the intestinal mucosa from aggressive actions of potentially dangerous substances and pathogens to prevent harmful bacteria from being passed on to the foal. It consists entirely of safe and natural ingredients rather than drugs. The dietary supplement of the present invention is orally administrable, thereby making its dispensation a simple matter.

The dietary supplement of the present invention is stable and has a long shelf life, and requires no special care to be provided by the user throughout its shelf life prior to usage. The dietary supplement of the present invention is also inexpensive relative to previously known nutritional supplements given to mares and other animals prior to parturition, thereby enhancing its market appeal and affording it the broadest possible market. Finally, all of the aforesaid advantages and objectives of the dietary supplement of the present invention and its method of administration are achieved without incurring any substantial relative disadvantage.

DESCRIPTION OF THE DRAWINGS

These and other advantages of the present invention are best understood with reference to the drawings, in which:

FIG. 1 is a somewhat schematic drawing of a horse showing the anatomy of the horse's digestive tract.

DETAILED DESCRIPTION OF THE PREFERRED EMBODIMENT

Prior to a discussion of the dietary supplement of the present invention and methods of making and administering it, it is helpful to briefly discuss the anatomy of the digestive system of a horse. Referring to the FIGURE, a side view of a horse 20 is illustrated, schematically illustrating the digestive tract of the horse. The digestive tract of the horse 20 may be separated into a foregut, which is indicated generally by the reference numeral 22, and a hindgut, which is indicated generally by the reference numeral 24.

The digestive tract of the horse 20 begins at its mouth 26, and sequentially extends through an esophagus 28 into a stomach 30 and then into a small intestine 32, which together constitute the foregut 22 of the horse 20. The foregut 22 of the horse 20 constitutes approximately thirty-five to forty percent of the relative capacity of the digestive tract of the horse 20.

From the small intestine 32, the digestive tract extends through a cecum 34, a large colon 36, and a small colon 38 which terminates in a rectum 40. These elements of the digestive tract of the horse 20 together constitute the hindgut 24 of the horse 20. The hindgut 24 constitutes approximately sixty to sixty-five percent of the relative capacity of the digestive tract of the horse 20.

In its preferred implementation, the preferred embodiment of the dietary supplement of the present invention includes four ingredients which are mixed together to manufacture the dietary supplement. These ingredients are: 1. a polar lipid supplement that provides antioxidants and galactolipids; 2. a soluble fiber that stimulates the immune system and slow the transit of feed through the digestive system; 3. one or more nutricines that provide a beneficial effect on the digestive system; and 4. one or more nutricines that absorb and/or eliminate pathogenic bacteria and/or mycotoxins in the digestive tract.

Each of these ingredients will be discussed separately below, together with a description of its preferred composition, alternative compositions, the preferred amount of the composition used in the dietary supplement, and the range of the amount of the composition which may be used in the dietary supplement. During the following discussion of the ingredients of the dietary supplement of the present invention, it will rapidly become apparent to those skilled in the art that the benefits achieved by the dietary supplement of the present invention are greater than the sum of the individual benefits of each of the dietary supplement's ingredients.

The first ingredient of the dietary supplement of the present invention is a polar lipid supplement that provides galactolipids and antioxidants. Galactolipids are polar lipids (membrane lipids) that protect intestinal tissue and help carry and increase the bioavailability of nutrients (such as nucleotides and functional proteins (immunoglobulins and lactoalbumins)) to the body. Antioxidants can scavenge the dangerous free radicals that damage cell tissue and reduce the cell immunity. Thus, it is desirable to have a polar lipid supplement which is high in both galactolipids and antioxidants. Polar lipids occur naturally in vegetable oils.

Polar lipids are emulsifiers, allowing water-soluble nutrients and fat-soluble nutrients (such as vitamins A, D, E, & K) to be easily absorbed in the bloodstream. Polar lipids thus provide a versatile delivery vehicle for drugs and nutrients. Studies have shown that polar lipids can increase the bioavailability of dissolved drugs. In addition to their use as emulsifiers, polar lipids physically augment the protective effect of mucus in the digestive tract. They also help to reinforce the so-called "tight junctions" between the enterocytes that line the digestive tract. Finally, vegetable oils contain tocopherols and trienols, which are powerful antioxidants, sweeping free radicals out of the system.

There are a number of potential sources of polar lipids that may be used to provide antioxidants and galactolipids in the dietary supplement of the present invention. In the preferred embodiment, oat oil is used due to the fact that oat oil has more polar lipids per unit volume than any other any other polar lipid source. Oat oil is also an excellent source of antioxidants. While other oils, especially those containing phospholipids, can be used instead of oat oil, the galactolipids found in plant material are more versatile than the phospholipids and are thus preferred. Other oils that are also good sources of polar lipids are sunflower oil, soybean oil, olive oil, palm oil, corn oil, rapeseed oil, linseed oil, etc.

In the preferred embodiment of the dietary supplement of the present invention, the polar lipid supplement is made of different viscosity components of oat oil (or other polar lipid ingredients) in order to affect the ultimate character of the dietary supplement. Like most oils, oat oil may come from multiple extractions, with the typical extraction process crushing the oats and treating them with an extraction agent such as hexanol. While there are a variety of sources for oat oil, one commercial source for the oat oil is Swedish Oat Fiber AB in Gothenburg, Sweden, which manufactures a high grade of oat oil. In addition, to the oat oil, sunflower oil (which is a thinner oil and does not contain as high an amount of polar lipids) may be added as a carrier to produce a liquid or paste form of the dietary supplement of the present invention.

The second ingredient of the dietary supplement of the present invention is a soluble fiber that is a powerful immune system stimulator, and that also slows the transit of feed through the digestive system. The soluble fiber used is an oligosaccharide (a soluble fiber) that is found in oats and yeasts, and which stabilizes blood sugar and reduces the dangerous cholesterol fraction in the blood. This soluble fiber also activates the protective macrophages to fight infections and thereby stimulate the immune system. It is a nutrient for the beneficial bacteria of the hindgut, helping the bacteria produce the micronutrients that are required by the host body.

There are a number of potential sources of soluble fiber that may be used in the dietary supplement in the dietary supplement of the present invention. In the preferred embodiment, the soluble fiber used is beta-glucan that is derived from oats. Other soluble fibers that are also good sources of beta-glucan are those derived from barley or soybeans. Beta-glucan is widely available from a large number of different suppliers, and may be milled as a flour.

The third ingredient of the dietary supplement of the present invention is one or more nutricines such as surfactant amino acids which exert beneficial effects on a stressed digestive system. There are two amino acids that are used in the preferred embodiment of the dietary supplement of the present invention, namely L-threonine and L-glutamine, which are both naturally produced amino acids which are produced by breaking down a protein.

L-glutamine is a naturally produced nonessential amino acid which is produced by breaking down protein. L-glutamine is the most abundant amino acid in the bloodstream, and is primarily formed and stored in skeletal muscle and the lungs (and is the primary fuel of enterocytes, essential in their growth, reproduction, and repair). L-glutamine also increases growth hormones, and when ingested has a substantial effect on maintaining and increasing mucosal integrity, including enhancing the integrity of the mucous gut membrane. L-glutamine functions to "kick start" the formation of nucleotides, which are involved in the production of cell tissue and the maturation of the intestinal mucosa, and are directly involved in the immune processes and the energy systems. A diet deficient in glutamine will most likely also likely result in a deficiency in nucleotide formation.

Instead of using L-glutamine, the peptide-bonded form of glutamine, which potentially presents advantages over L-glutamine, may be used. Much of the ingested L-glutamine does not make it into the blood stream or muscle tissue, since anywhere between fifty and eighty-five percent of the L-glutamine is used immediately by the intestines, liver, and the immune system. Glutamine peptide is more stable and is better absorbed and utilized, enhancing the availability of glutamine in the bloodstream and making it more readily available to muscle tissue. Approximately half as much glutamine peptide is required when compared to the amount of L-glutamine.

L-threonine is a naturally produced essential amino acid which is produced by breaking down protein. L-threonine makes up collagen, elastin, and enamel protein, assists in metabolism and assimilation, and aids the digestive system by increasing the integrity of the mucous gut membrane. L-threonine has also been observed by the inventors to have a synergistic effect with beta-glucan in further slowing motility through the stomach. Thus, L-threonine and L-glutamine both act to protect the inside wall of the stomach by enhancing the integrity of the mucous gut membrane. L-threonine and L-glutamine are widely available from a large number of different suppliers, and are also powders.

The fourth ingredient of the dietary supplement of the present invention is one or more nutricines that are designed to absorb and eliminate pathogens (i.e., bacteria) and/or mycotoxins in the hindgut (the intestines and the colon). One of the additional ingredients used in the preferred embodiment is a pathogenic bacteria absorbant material that attracts bacteria and passes through the digestive system together with the absorbed pathogenic bacteria in the feces. Another additional ingredient used in the preferred embodiment is a mycotoxin absorbant nutricine that absorbs or soaks up mycotoxins in the hindgut.

These nutricines preferably consists of mannan oligosaccharides (MOS), which are complex sugars that are used to bind pathogens and, at the same time, nourish beneficial bacteria. Mannan oligosaccharides bind to attachment sites on pathogenic bacteria, preventing the pathogenic bacteria from binding to receptors in the enterocyte membrane. The mannan oligosaccharides are naturally derived from the cell wall of *saccharomyces cerevisiae* (brewer's yeast), a yeast extract, although other sources of mannan oligosaccharides are also acceptable. These nutricines may be made from yeast cell wall, and may include both a non-estrified yeast cell wall pathogenic bacteria absorbant nutricine as well as an estrified yeast cell wall mycotoxin absorbant nutricine.

The pathogenic bacteria absorbant material that attracts bacteria and passes through the digestive system together with the absorbed pathogenic bacteria may be a pathogenic bacteria absorbant such as the material marketed under the trademark BIO-MOS by Alltech, Inc. The pathogenic bacteria absorbant material attracts bacteria and passes through the digestive system together with the absorbed pathogenic bacteria in the feces. The mycotoxin absorbant nutricine used to absorb or soak up mycotoxins in the hindgut may be a mycotoxin absorbant material marketed under the registered trademark MYCOSORB by Alltech, Inc. The mycotoxin absorbant nutricine absorbs or soaks up mycotoxins in the hindgut.

Another pathogenic bacteria absorbant nutricine that could instead be used include the material marketed under the trademark BIOSAF by S.I. Lesaffre of Cedex, France. Other mycotoxin absorbant nutricines that could instead be used include the material marketed under the trademark MYCOFIX PLUS by Biomin Distribution, Inc. and the material marketed under the trademark D-MYCOTOC by Kanzy Medipharm, Inc. of Brossard, Canada. Another nutricine that could be used instead of BIO-MOS and MYCOSORB is the material marketed under the trademark NUTRIMOS (which is essentially a combination of Mannan Oligosaccharide ("MOS") for bacterial issues and gluco-mannans for mycotoxin issues, thereby essentially combining the two Alltech products) by S.I. Lesaffre.

These four ingredients of the dietary supplement of the present invention thus provide high galactolipids and antioxidants, stimulate the immune system, provide a beneficial effect on the digestive system, and absorb and/or eliminate pathogenic bacteria and/or mycotoxins in the digestive tract. In addition to these four ingredients, in the preferred embodiment additional ingredients may be included in the dietary supplement of the present invention to further enhance its capacities.

An optional active ingredient that may be included in the dietary supplement of the present invention consists of a supplement which contains nucleotides, which are vital components to metabolic functions which control the regulatory pathways in growth and provide immunity to diseases. Nucleotides, which are building blocks of DNA or RNA consisting of a nitrogenous base, a phosphate molecule, and a sugar molecule (deoxyribose in DNA and ribose in RNA). Depending upon the sugar, the nucleotides are called deoxyribonucleotides or ribonucleotides. Millions of nucleotides are linked to form a DNA molecule (and thousands of nucleotides are linked to form an RNA molecule).

There are several sources for nucleotides, the best of which are derived from brewer's or baker's yeast. Two sources of products containing nucleotides are S.I. Lesaffre, and Alltech, Inc. The Lesaffre product is marketed under the trademark YEAST CELL EXTRACT (2006), and contains approximately fifteen percent nucleotides. The Alltech product is marketed under the registered trademark NUPRO, and contains between five and seven percent nucleotides. Generally, products having higher nucleotide levels are preferred over products having lower nucleotide levels. Nucleotides are also contained in mannan oligosaccharide, which typically contains approximately five percent nucleotides.

The balance of the protective and the invasive factors of the intestines determines the health of the gut. Maintenance of the mucosal bloodflow is one of the most critical and important protective factors, and is believed to be enhanced by nucleotides. The gut wall have a number of minute finger-shaped processes of the mucous membrane called villi that serve in the absorption of nutriments, with crypts located between adjacent villi. Proper nutritional uptake, the height of the villi, and increased mucosal bloodflow are all related, and reduced mucosal bloodflow will result in shortened villi and shallower crypts, which in turn results in a decreased level of nutritional uptake. Animal studies have demonstrated that dietary nucleotides increase villi height and mucosal bloodflow, which in turn increases the uptake of nutrients into the body and the effectiveness of other nutritional elements.

Finally, there is a non-active ingredient which is added to the dietary supplement of the present invention as an emulsifier in order to thicken the dietary supplement and prevent its constituents from separating. The emulsifier used in the dietary supplement in the preferred embodiment is guar gum, which also has thickening and stabilizing properties. Other emulsifiers having appropriate properties could be used instead of the guar gum, such as carrageenen and agar.

Optionally, the dietary supplement of the present invention could also include one or more vitamins and minerals which contribute to the final dietary supplement in their capacity as antioxidants and/or enhance the total nutritional qualities of the dietary supplement. Such additional ingredients may include Vitamin E and/or various minerals such as Selenium, Copper, Manganese, Zinc, and Chromium. These minerals may be added in the form of Selenium Yeast, Copper Yeast, Manganese Yeast, Zinc Yeast, and Chromium Yeast, respectively, all of which are available from Alltech, Inc. as well as other providers.

The range of amounts of oat oil or other polar lipid supplement is between approximately twenty percent and eighty percent of the dietary supplement by weight. The preferred range of amounts of oat oil or other polar lipid supplement is between approximately twenty-five percent and fifty percent of the dietary supplement by weight. The most preferred amount of oat oil or other polar lipid supplement is approximately forty-one percent of the dietary supplement by weight.

The range of the carrier oil, which is sunflower oil in the preferred embodiment, is between approximately zero percent and forty percent of the dietary supplement by weight. The amount of the carrier oil that is used depends upon the desired consistency of the product, with approximately twenty-two and eight-tenths of a percent being used in the most preferred embodiment, which may be used to produce a paste.

The range of amounts of beta-glucan or other soluble fiber is between approximately ten percent and fifty percent of the dietary supplement by weight. The preferred range of amounts of beta-glucan or other soluble fiber is between approximately fifteen percent and thirty-five percent of the dietary supplement by weight. The most preferred amount of beta-glucan or other soluble fiber is approximately twenty-eight percent of the dietary supplement by weight.

The nutricines that provide a beneficial effect on the digestive system will collectively be between approximately two percent and thirteen percent of the dietary supplement by weight. The preferred amount of the nutricines that provide a beneficial effect on the digestive system is approximately three and six-tenths percent of the dietary supplement by weight.

The range of amounts of L-glutamine is between approximately one percent and five percent of the dietary supplement by weight. It is believed that less than one percent of L-glutamine will result in little or no efficacious result. The preferred amount of L-glutamine is approximately one and six-tenths percent of the dietary supplement by weight. If glutamine peptide is used instead of L-glutamine, half of these amounts would be required. The range of amounts of L-threonine is between approximately one percent and five percent of the dietary supplement by weight. The preferred amount of L-threonine is approximately two percent of the dietary supplement by weight.

The nutricines that absorb and/or eliminate pathogenic bacteria and/or mycotoxins in the digestive tract will collectively be between approximately two percent and twenty percent of the dietary supplement by weight. The preferred amount of the nutricines that absorb and/or eliminate pathogenic bacteria and/or mycotoxins in the digestive tract is approximately four percent of the dietary supplement by weight.

The range of the pathogenic bacteria absorbant material that attracts bacteria and passes through the digestive system is between approximately one percent and ten percent of the dietary supplement by weight. The preferred amount of the pathogenic bacteria absorbant material that attracts bacteria and passes through the digestive system is approximately two percent of the dietary supplement by weight. The range of the mycotoxin absorbant nutricine used to absorb or soak up mycotoxins in the hindgut is between approximately one percent and ten percent of the dietary supplement by weight. The preferred amount of the mycotoxin absorbant nutricine used to absorb or soak up mycotoxins in the hindgut is approximately two percent of the dietary supplement by weight.

Finally the relative weight of the guar gum is between zero percent and approximately two percent of the dietary supplement by weight. The preferred amount of the guar gum is approximately six-tenths of one percent of the dietary supplement by weight.

The range of amounts of the optional nucleotides is between approximately one-half percent and ten percent of the dietary supplement by weight. If the nucleotides are used in the dietary supplement, the preferred amount is approximately one percent of the dietary supplement by weight. These percentages are based upon use of the Yeast Cell Extract (2000) from Lesaffre, and will have to be adjusted proportionately upwardly if another Yeast Cell Extract having a lower concentration of nucleotides is used.

If Vitamin E is used, the preferred amount would be approximately two-tenths percent of the dietary supplement by weight. If used, the preferred amount of each of the selenium yeast, the copper yeast, the manganese yeast, the zinc yeast, and the chromium yeast would be approximately one-tenth of one percent of the dietary supplement by weight.

The dietary supplement of the present invention can be manufactured as a solid (typically pelleted), as a granulated solid, as a powder, as a paste, or as a liquid. In order to manufacture it as a solid, a small amount of oat flour or oat bran (or substitutes therefor) may be added to thicken it. The pelleting procedure should be performed at low temperature, preferably not higher than 65 degrees Celsius, and may optionally include approximately twenty percent by weight of grass meal and/or Alfalfa meal. By adding a higher percentage of oat flour or oat bran while stirring the mixture, a granular form of the supplement may be manufactured. This granular form can be sprinkled on feed, or added to a liquid. By adding still more flour while stirring the mixture, a powder form of the supplement may be manufactured.

By adding more oil (oat oil, sunflower oil, or another oil), the mixture can be brought to a paste having the consistency of peanut butter. In the paste form, the dietary supplement of the present invention may be stored in gelatin capsules (as liquid-filled softgel capsules), which also provide for a consistent dosage of the dietary supplement. By adding still more oil, it can be made into a viscous liquid which can be poured onto feed.

The dietary supplement of the present invention may be administered either by adding it to feed or by feeding it directly as a dietary supplement. In the preferred embodiment, the dietary supplement is administered once or twice daily. It may be manufactured either as a liquid, in which case it can be added to feed which is then fed to a horse, or as a liquid or paste and stored in a gelatin capsule (as gelcaps), which makes for a consistent and uniform dosage of the dietary supplement. If manufactured as a paste, it can also be orally administered using a dose syringe.

Alternatively, the dietary supplement of the present invention may be manufactured by pelleting it together with grass meal and/or Alfalfa meal. The pelleting procedure should be performed at low temperature, preferably not higher than 65 degrees Celsius, to avoid the degradation or destruction of the beneficial ingredients, particularly those contained in the whey protein concentrate. The ingredients of the dietary supplement should be approximately twenty percent by weight of the total weight of the pellets.

It is desirable that the dietary supplement of the present invention is taken on a regular basis, which in the preferred embodiment is daily in order to maintain an optimal level of the ingredients in the digestive tract. The preferred dosage for mares is approximately one ounce of the dietary supplement of the present invention once daily, which may be administered together with hard feed (the grain diet which produces ulcerations), preferably at an evening feeding. Administration of the dietary supplement may be done using dose syringes, and horses typically willingly accept the dietary supplement (with its oat base, horses like its taste and willingly take it as a treat).

The weight of the dietary supplement varies according to its form, with the paste form having a specific density of approximately 0.8, and the granular or flour forms having a specific density of between 0.5 and 0.6. Thus, the preferred dosage of the dietary supplement of the present invention may be varied accordingly.

It will be readily apparent to those skilled in the art from the preceding discussion of the ingredients of the dietary supplement of the present invention and their interaction that the benefits achieved by the dietary supplement of the present invention is substantially greater than the sum of the benefits of each of the dietary supplement's ingredients separately.

Clinical Investigation

An experiment was conducted to measure the effect on immunity of twenty-four thoroughbred mares in the state of Kentucky when the dietary supplement of the present invention was added to the daily diet ninety days prior to foaling. Since colostrum immunoglobulin levels are correlated to blood immunoglobulin levels in mares, blood immunoglobulin levels are thus a good indication of mare colostrum immunoglobulin levels. Further, since a high colostrum immunoglobulin level is critical for the success of passive transfer of immunity to foals, blood immunoglobulin levels can therefore be a good predictive indicator for foal immunity. In order to determine the effect of the dietary supplement of the present invention on mare colostrum immunoglobulin, blood samples were obtained and analyzed for blood immunoglobulin (IgG) using standard methods at a large veterinary medicine clinic in Lexington, Ky.

The twenty-four thoroughbred mares located on three breeding farms in central Kentucky were split into two groups of thirteen mares each. The mares in one group received the dietary supplement of the present invention in the paste form at one ounce per mare per day. The mares in the control group did not receive the dietary supplement of the present invention. All mares in the study received adequate nutrition, were of good health, and foaled normally. Colostrum samples were taken within eight hours post-foaling and were analyzed by radial immunodiffusion assay ("RID") at the large equine veterinary medicine clinic in Lexington, Ky. Differences in population means were analyzed for significance using the Student T test.

Blood Work Results

| Horses Receiving the Dietary Supplement | | Horses Not Receiving the Dietary Supplement | |
| --- | --- | --- | --- |
| HORSE | Colostrum IgG | Horse | Colostrum IgG |
| Horse 1 | 17605 | Horse 13 | 4440 |
| Horse 2 | 24555 | Horse 14 | 100 |
| Horse 3 | 17065 | Horse 15 | 4315 |
| Horse 4 | 16940 | Horse 16 | 11550 |
| Horse 5 | 13740 | Horse 17 | 7855 |
| Horse 6 | 13085 | Horse 18 | 6975 |
| Horse 7 | 17191 | Horse 19 | 5605 |
| Horse 8 | 9409 | Horse 20 | 5660 |
| Horse 9 | 2365 | Horse 21 | 11967 |
| Horse 10 | 7970 | Horse 22 | 11315 |
| Horse 11 | 16020 | Horse 23 | 2685 |
| Horse 12 | 12512 | Horse 24 | 12467 |
| Average | 14038 | Average | 7078 |

The mares that received the dietary supplement of the present invention had a significant (p=0.02) ninety-seven percent improvement in colostrum immunoglobulin values as compared to the mares that did not receive the dietary supplement of the present invention. For the mares on the dietary supplement of the present invention, measured values of colostrum immunoglobulin (IgG) values ranged from 2365 to 24555 with an average of 14038 milligrams per deciliter, while the mares in the control group had measured values of colostrum immunoglobulin (IgG) values from 100 to 12467 with an average of 7078 milligrams per deciliter. The colostrum immunoglobulin (IgG) values for the mares in the control group are considered to fall within the average range for horses of approximately 7000 milligrams per deciliter.

The mares that received the dietary supplement of the present invention were shown to have very good immunity as measured by colostrum immunoglobulin quality, nearly twice that of the negative control group whose colostrum immunoglobulin would be considered average. The dietary supplement of the present invention clearly helped the mares receiving the dietary supplement to produce very high quality colostrum, which provides major benefits for foals consuming this colostrum. While the mode of action of the dietary supplement of the present invention is not exactly determined, it is believed that by removing digestive tract and immune-related stresses on the mare, the mares receiving the dietary supplement of the present invention were healthier overall with less stressed immune systems, and as such were capable of directing more of their resources towards production of quality colostrum. Clearly, both a health benefit and an economic benefit are obtained for these mares and their foals by feeding the mares the dietary supplement of the present invention during gestation.

It may therefore be appreciated from the above detailed description of the preferred embodiment of the present invention that it teaches a dietary supplement that provides a substantial increase in the levels of immunoglobulin antibodies in the colostrum or "first milk" produced by a mare immediately upon parturition. The dietary supplement of the present invention provides as much as a ninety-two percent increase in the level of immunoglobulin antibodies in the colostrum. The dietary supplement of the present invention also provides a substantial enhancement in the passive transfer of immunoglobulin antibodies from the mare to the foal through ingestion of the colostrum.

The dietary supplement of the present invention strengthens the immune system of the mare during gestation. The dietary supplement of the present invention also helps to protect the intestinal mucosa from aggressive actions of potentially dangerous substances and pathogens to prevent harmful bacteria from being passed on to the foal. It consists entirely of safe and natural ingredients rather than drugs. The dietary supplement of the present invention is orally administrable, thereby making its dispensation a simple matter.

The dietary supplement of the present invention is stable and has a long shelf life, and requires no special care to be provided by the user throughout its shelf life prior to usage. The dietary supplement of the present invention is also inexpensive relative to previously known nutritional supplements given to mares and other animals prior to parturition, thereby enhancing its market appeal and affording it the broadest possible market. Finally, all of the aforesaid advantages and objectives of the dietary supplement of the present invention and its method of administration are achieved without incurring any substantial relative disadvantage.

Although the foregoing description of the dietary supplement of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

Appendix—Digestive Tract Ulcers in Horses

This appendix discusses a consequence of the somewhat unique digestive tract anatomy of horses, namely a high incidence of digestive tract ulcers in horses. In the case of humans and most other animals, gastric acid is secreted in the stomach in response to eating. In contrast, horses have developed over millennia as trickle feeders (eating slowly but more or less continuously over most of the day), and their digestive systems are geared for such a diet, with a continuous production of gastric juices and bile secretion into the foregut from the liver. Thus, the stomach of a horse may be thought of as an acid pump that produces gastric acid more or less continuously through the day, whether or not the horse is being fed.

The incidence of digestive tract ulcers in performance horses has risen most sharply, from approximately twenty percent in 1920 to approximately ninety percent or better in the last decade. In racehorses, for example, as much as ninety-seven percent of the racehorse population has been reported to have digestive tract ulcers, with the percentage of show horses having digestive tract ulcers lagging only slightly behind. Even performance horse foals have been inflicted with this condition, with approximately sixty percent of performance horse foals having digestive tract ulcers. While pleasure horses have a lower incidence of digestive tract ulcers than show horses, the increasing incidence of digestive tract ulcers in the last two decades has been significant for all segments of the horse population, including pleasure horses.

A recent scientific study of a random cross-section of horses indicated that approximately fifty-five percent of them had gastric ulcers and forty percent of them had colonic ulcers. The incidences of gastric and colonic ulcers were not identical, meaning that some horses had only gastric ulcers and other horses had only colonic ulcers. However, a large percentage of the horses that had colonic ulcers also had gastric ulcers, with less than thirty percent of the horse population as a whole not having either gastric or colonic ulcers. As mentioned above, the incidence of digestive tract ulcers for show horses and racehorses is even higher than these statistics for the general horse population.

The direct cause of digestive tract ulcers in horses appears to be excess stomach acid, as is the case with humans and other animals. Excess stomach acid can "eat" through the protective lining of the stomach and damage the interior surface of the stomach, causing gastric ulcers. In humans, it is believed that the prevalent factor in the development of stomach ulcers is the *helicobacter pylori* bacteria. However, the *helicobacter pylori* bacteria has not been isolated from horse stomachs, and thus is not believed to be a factor in the development of digestive tract ulcers in horses.

The inside wall of the stomach is protected by a mucous gut membrane lining which is a fatty layer containing polar lipids. When there is no food contained in the horse's stomach, the gastric acid will act on the mucous gut membrane lining the inside wall of the stomach, oxidizing the cells of the gut lining and burning them up. These burned-up gut lining cells are sloughed off, and pass through the digestive system, exposing the gut wall to the gastric acid and allowing gastric ulcers to form. This condition is known as equine gastric ulcer syndrome ("EGUS").

In addition, there is a continuous peroxidation and oxidation of proteins and lipids which results in the formation of free radicals. As the fatty cells containing polar lipids in the mucous gut membrane are oxidized and burned off, free radicals are created. These free radicals can break down muscle tissue, and have been shown to have an adverse affect on the performance of horses. Thus, it is readily apparent to those skilled in the art that digestive tract ulcers have a substantial adverse effect on performance horses, and can prevent performance horses from achieving their true potential.

In the case of humans, the production of saliva and its mixing with ingested foodstuffs initiates the digestion process since human saliva includes the enzyme amylase, which breaks down starch into sugar. Horse saliva does not contain amylase or any other enzyme that can initiate the digestion process. However, horse saliva does contain a buffering agent that can help to neutralize gastric acid contained in the horse's stomach.

Another unique feature of horses' digestive tracts is the presence of a large microbial population in the hindgut. These microorganisms are responsible for the fermentation of the residues of the digestive process and absorption of digested feed, and have the ability to utilize the cellulose that is present in forages. The anatomy of the hindgut, which has a number of folds contained therein, causes the passage of ingested feed to pass through relatively slowly as compared to the rate of passage of ingested feed through the foregut. While this is advantageous when digesting roughages such as forage, it can also predispose a horse to digestive upsets when insufficient roughage is contained in the ingested feed.

In addition to the unique anatomy of horses' digestive tracts, there are several other factors which also appear to increase the incidence of digestive tract ulcers in horses. These factors include feeding practices, physical stress (including the stress from being in a stable as much as twenty-three hours of the day), and medications being given to the horses. In the case of performance horses, two additional factors which can also increase the incidence of digestive tract ulcers are the intensity of training and the initiation of training of foals at a young age, the latter of which is particularly prevalent with racehorses. However, it has been determined by the inventors that while all of these factors are significant, the primary factors are the unique physiology of the horse digestive tract and modern feeding practices, with the other factors acting to further exacerbate a condition which is essentially caused by two aforesaid primary factors.

Thus, other than the unique physiology of horses' digestive tracts, the primary factor leading to the high incidence of digestive tract ulcers in horses is diet-related, and is a consequence of a drastic change in the diet of most horses. Until the relatively recent past, horses for the most part had been allowed to be free-range grazers, with a diet that consisted primarily of forage. However, beginning in the 1920's, fewer and fewer horses have had the opportunity to free range graze, or even to have the freedom to eat hay or other forage during much of the day. Instead, most horses are fed diets that are high in grains, with forage either being reduced to minimal levels or eliminated entirely from the horses' diets. Typical feeding schedules for horses are twice or three times daily, generally with feedings in the morning and the evening, and a third feeding at midday, mimicking a human diet. With this change in diet, the incidence of digestive tract ulcers in horses has increased tremendously, especially in performance horses (including both racehorses and show horses), which also have additional stresses that exacerbate the problem caused by the consequences of a low forage diet and the nature of the digestive tract of horses.

When horses are allowed to eat forage (which is essentially high fiber, low nutrition material), as they have evolved to do, they typically eat for approximately sixteen hours a day. If allowed to graze, they will begin feeding in the early morning, and will continue to feed until well after dark, nibbling, chewing, swallowing, and digesting slowly to keep their small stomachs from becoming empty. Given free choice, horses will search out and find a balanced diet typically consisting of grasses, berries, and leaves, which provide a balance of essential microminerals in addition to basic volume and energy requirements. The constant chewing produces saliva that neutralizes the gastric acid. (Saliva contains positive ions ("cations") which counteract the negative ions ("anions") of gastric acid.)

Most horses today are neither kept in pastures where they can eat forage all day long, nor fed forage in a stable. Instead, stabled horses are typically fed a concentrated, low volume diet of grain products with relatively small quantities of hay or forage being available to them, and then only intermittently. With regard to racehorses and other performance horses, the diet bears even less resemblance to a forage diet. Racehorses are fed a high-energy diet to maximize muscle growth and activity levels; this diet typically consists of a mixture of grains, molasses, nutrients, and feed additives, usually with minimal hay in the form of one or two flakes with each meal.

The concentrated, low volume diet of grain products is generally fed to the horses three times (or in some cases only twice) a day, and the horses generally eat it rapidly. When fed to horses, such a low volume diet of grain products passes through their stomachs relatively quickly. Since this type of diet is concentrated and of high quality, horses fed such a diet are not nutritionally underfed; rather, they are "behaviorally" underfed. Diets that are low in fiber and high in starch increase the potential that starches which are not digested in the foregut will enter the hindgut, where they will rapidly ferment, causing a rapid reduction in the pH level in the hindgut and a volatile fatty acid imbalance. The acidic environment created in this manner has a direct effect on the balance of microflora (the huge community of microorganisms which forms a complex and dynamic ecosystem within the hindgut) within the hindgut.

One consequence of such a diet is that relatively little of the buffering saliva reaches the horses' stomachs. This is due to the fact that the buffering capacity is determined mainly by the volume of saliva that is produced while horses are eating. For a given weight of concentrated food such as grain products, the volume of saliva produced is less than half the volume of saliva that would be produced by the same weight of forage. Thus, it will at once be appreciated by those skilled in the art that, except for the relatively brief time when horses are eating and shortly thereafter, their stomachs will be empty, with no buffering saliva. Since horses' stomachs are not adapted to such intermittent feeding, they will constantly be bathed with gastric acid, causing gastric ulcers.

Since the gastric acid from the stomach can flow into the hindgut, it is also possible for horses to have colonic ulcers, particularly ulcers in the large intestine, typically in the right ventral colon. The consequences of colonic ulcers in horses are caused or exacerbated due to the presence of pathogens and mycotoxins in the hindgut. These pathogens and mycotoxins can fasten themselves onto the lesions and cause infections in the walls of the hindgut. The pathogens and mycotoxins are ingested by horses in their feed, and are metabolites of funguses growing on the feed. Generally, the pathogens and mycotoxins will pass through horses' digestive tracts unless there are colonic ulcers that are susceptible to the pathogens and mycotoxins. Pathogens and mycotoxins can cause severe problems including digestive, reproductive, neurological, and athletic problems, as well as chronic obstructive pulmonary disease ("COPD") in horses. For example, colonization on sites of colonic ulcers caused by pH changes and attack by acids can cause transit of mycotoxins into the blood, and eventually may result in damage to the liver and even renal dysfunctions.

There are three solutions to the problem of digestive tract ulcers in horses that have been utilized in the art, none of which have been satisfactory. The first known solution is the use of antacids, also referred to euphemistically as "gastric ulcer transnutrients." Antacids (typically mixtures of magnesium and aluminum hydroxide) are administered to temporarily neutralize acid in the stomach. However, antacids are treating the symptom rather than the problem, and are relatively ineffective due to the fact that they pass rapidly through horses' stomachs, and thus an increase in pH in the stomach that is achieved with antacids is typically of short duration. In addition, since gastric acid is constantly produced by horses, it will at once be appreciated by those skilled in the art that antacids are substantially ineffective in treating digestive tract ulcers in horses.

The second known solution is the use of drugs, which are administered to inhibit the production of gastric acid. These are presently three classes of drugs which are used for this purpose: histamine type-2 antagonists such as cimetidine (available from GlaxoSmithKline under its registered trademark TAGAMET) and ranitidine (available from Pfizer under its registered trademark ZANTAC or from Ranvet under its registered trademark ULCERGUARD), or proton pump inhibitors such as omeprazole (available from Astra AB under its registered trademark GASTROGARD). These drugs claim to be effective in curing gastric ulcers in three to four weeks, but are very expensive. It is apparent to those skilled in the art that the temporary change in the stomach environment is highly unlikely to result in complete restoration of health during treatment.

They do have several disadvantages in addition to their expense, the most problematic of which is that once they are discontinued the digestive tract ulcers will usually recur quickly, requiring another round of treatment. In some instances, veterinarians may find it necessary to prescribe continuing treatment with one of these medications, which becomes extremely expensive. In addition, some of these drugs must be withheld prior to racing in the case of racehorses. Another profound disadvantage is that these drugs interfere with proper digestion by changing the natural pH balance, which results in the treated horses being in less than optimum condition.

The third, and most effective, known solution is the only natural solution known at present—rest and a diet of forage. This means allowing horses to return to pasture, and a diet of hay and other forage. It is the only real solution that has been known in the art, and it is the universal prescription to provide a complete return to health. For performance horses, it may inhibit the ability of the horses to compete; for owners of other horses it represents an ideal solution that is simply not possible. Accordingly, rest and diet does not represent an optimal solution for many horses and their owners.

Returning now to the discussion of foal nutritional system development, a foal significantly changes its suckling habits about ten days to two weeks after birth (sometimes much earlier, even as early as two to three days after birth). When the foal starts nibbling and even eating the mare's feed, it is important that this be observed, and that the mare not be allowed to have a high starch diet that could affect the foal's gastrointestinal function, which could in turn lead to a lowering of the pH, increasing acidity in the stomach and damaging the intestinal mucosa, resulting in gastric ulcers. Amazingly, the incidence of gastric ulcers in foals at three to four weeks after birth have been shown to be as high as approximately fifty percent.

The early management of the foal's nutritional intake will determine the later status of its gastrointestinal tract, and the balance of the protective and the invasive factors of the intestines will similarly determine the health and the maturation process of the gut. Maintenance of the mucosal bloodflow is one of the most critical and important protective factors. The gut wall of horses have a number of minute finger-shaped processes of the mucous membrane called villi that serve in the absorption of nutriments, with crypts located between adjacent villi. Proper nutritional uptake, the height of the villi, and increased mucosal bloodflow are all related, and reduced mucosal bloodflow will result in shortened villi and shallower crypts, which in turn results in a decreased level of nutritional uptake.

Other important factors that determine the health and the maturation process of the gut are the bicarbonate and mucous production, and the growth and the restitution of the epithelium of the foal's stomach. The bloodflow that delivers vital nutrients and oxygen to the intestinal membrane also takes away invasive products such as hydrogen ions and toxins. Other invasive products are digestion products such as gastric juices, enzymes, and bile salts, all of which are necessary in the normal digestion process, but which if present in excess can cause problems and can damage the intestinal wall.

What is claimed is:

1. A dietary supplement composition comprising:
   a polar lipid supplement that has been isolated from its natural source which polar lipid supplement is high in galactolipids and antioxidants;
   a soluble beta-glucan fiber source that has been fractionated from its natural origin which soluble beta-glucan fiber source exerts a beneficial effect on health;
   at least one amino acid that provides at least one beneficial effect on a digestive system; and
   at least one nutricine that absorbs and/or eliminates pathogenic bacteria and/or mycotoxins in the digestive tract consisting of mannan oligosaccharides;
   wherein said polar lipid supplement, said soluble beta-glucan fiber source, said at least one amino acid, and said at least one nutricine are present in respective amounts sufficient to cause the dietary supplement to exert a beneficial effect on the health of an equine.

2. A dietary supplement composition as defined in claim 1, wherein said polar lipid supplement contains lipids of oats.

3. A dietary supplement composition as defined in claim 1, wherein said polar lipid supplement comprises:
   oat oil.

4. A dietary supplement composition as defined in claim 3, additionally comprising:
   at least one oil selected from the group consisting of sunflower oil, soybean oil, olive oil, palm oil, corn oil, rape seed oil, and linseed oil.

5. A dietary supplement composition as defined in claim 1, wherein said soluble beta-glucan fiber source is derived from at least one ingredient selected from the group consisting of oats, barley, and soybeans.

6. A dietary supplement composition as defined in claim 1, wherein said soluble beta-glucan fiber source is derived from oats.

7. A dietary supplement composition as defined in claim 1 wherein said beta-glucan fiber source comprises oats.

8. A dietary supplement composition as defined in claim 1, wherein said at least one amino acid comprises:
   L-threonine.

9. A dietary supplement composition as defined in claim 1, wherein said at least one amino acid comprises:
   L-Glutamine.

10. A dietary supplement composition as defined in claim 1, wherein said at least one amino acid comprises:
    glutamine peptide.

11. A dietary supplement composition as defined in claim 1, wherein said at least one nutricine that absorbs and/or eliminates pathogenic bacteria and/or mycotoxins in the digestive tract is derived from a yeast cell wall product.

12. A dietary supplement composition as defined in claim 11, wherein said yeast cell wall product comprises:
a non-estrified yeast cell wall product.

13. A dietary supplement composition as defined in claim 11, wherein said yeast cell wall product comprises:
an estrified yeast cell wall product.

14. A dietary supplement composition as defined in claim 1, additionally comprising:
a nutricine that strengthens the immune system, comprising a supplement containing dietary nucleotides.

15. A dietary supplement composition as defined in claim 14, wherein said nutricine which enhances growth and/or strengthens the immune system is derived from brewer's or baker's yeast.

16. A dietary supplement composition as defined in claim 1, additionally comprising:
an emulsifier that thickens said dietary supplement composition and prevents the constituents of said dietary supplement composition from separating.

17. A dietary supplement composition as defined in claim 1, additionally comprising;
at least one mineral micronutritional additive.

18. A dietary supplement composition comprising:
a polar lipid supplement that has been isolated from its natural source which polar lipid supplement is high in galactolipids and antioxidants;
a soluble beta-glucan fiber source that has been fractionated from its natural origin in an amount sufficient to exert a beneficial effect on health;
at least one amino acid in an amount sufficient to provide at least one beneficial effect on a digestive system; and
at least one nutricine in an amount sufficient to absorb and/or eliminate pathogenic bacteria and/or mycotoxins in the digestive tract consisting of mannan oligosaccharides.

19. A method of making a dietary supplement composition, said method comprising:
providing a polar lipid supplement that has been isolated from its natural source which polar lipid supplement is high in galactolipids and antioxidants;
providing a soluble beta-glucan fiber source that has been fractionated from its natural origin which soluble beta-glucan fiber source exerts a beneficial effect on health;
providing at least one amino acid that provides at least one beneficial effect on a digestive system;
providing at least one nutricine that absorbs and/or eliminates pathogenic bacteria and/or mycotoxins in the digestive tract consisting of mannan oligosaccharides; and
mixing said polar lipid supplement, said soluble beta-glucan fiber source, said at least one amino acid, and said at least one nutricine together in relative amounts sufficient to cause the dietary supplement to exert a beneficial effect on the health of an equine.

* * * * *